United States Patent [19]

Steer

[11] Patent Number: 5,409,475
[45] Date of Patent: Apr. 25, 1995

[54] RETRACTILE PENIS DEVICE

[75] Inventor: Peter L. Steer, Sussex, England

[73] Assignee: E. R. Squibb & Sons, Inc., Princeton, N.J.

[21] Appl. No.: 209,683

[22] Filed: Mar. 10, 1994

Related U.S. Application Data

[63] Continuation of Ser. No. 548,696, Jul. 5, 1990, abandoned.

[30] Foreign Application Priority Data

Jul. 19, 1989 [GB] United Kingdom ............... 8916519

[51] Int. Cl.⁶ ..................... A61F 5/453; A61F 5/457
[52] U.S. Cl. ................................. 604/353; 604/352; 604/349; 4/144.3
[58] Field of Search ............... 604/327, 346, 347, 349, 604/352, 353, 332; 128/DIG. 24; 4/144.3, 144.1; 600/29

[56] References Cited

U.S. PATENT DOCUMENTS

| | | | |
|---|---|---|---|
| 2,484,356 | 10/1949 | Ribeiro et al. | 604/347 |
| 3,353,538 | 11/1967 | Carrigan | 128/295 |
| 3,835,857 | 9/1974 | Rogers et al. | 128/295 |
| 3,863,638 | 2/1975 | Rogers et al. | 128/295 |
| 3,916,902 | 11/1975 | Lineberger | 128/295 |
| 4,013,077 | 3/1977 | Ritota et al. | 128/295 |
| 4,022,213 | 5/1977 | Stein | 128/295 |
| 4,109,657 | 8/1978 | Carrington | 128/283 |
| 4,219,023 | 8/1980 | Galindo | 128/283 |
| 4,239,044 | 12/1980 | Pavlinch | 128/295 |
| 4,281,648 | 8/1981 | Rogers | 128/79 |
| 4,319,571 | 3/1982 | Winchell | 128/DIG. 24 X |
| 4,553,968 | 11/1985 | Komis | 604/349 |
| 4,568,340 | 2/1986 | Giacalone | 604/353 |
| 4,588,397 | 5/1986 | Giacalone | 604/349 |
| 4,655,755 | 4/1987 | Ruffini | 604/352 |
| 4,673,401 | 6/1987 | Jensen et al. | 604/353 |
| 4,713,066 | 12/1987 | Komis | 604/353 |
| 4,813,943 | 3/1989 | Smith | 604/329 |
| 4,820,291 | 4/1989 | Terauchi et al. | 604/349 |
| 4,834,731 | 5/1989 | Nowak et al. | 604/339 |
| 4,838,883 | 6/1989 | Matsuura | 604/349 |
| 4,886,510 | 12/1989 | Matsuura | 604/353 |

FOREIGN PATENT DOCUMENTS

| | | | |
|---|---|---|---|
| 32138 | 7/1980 | European Pat. Off. | |
| 119143 | 9/1984 | European Pat. Off. | |
| 0251502 | 1/1988 | European Pat. Off. | 604/332 |
| 2707408 | 8/1978 | Germany | 4/144.1 |
| 2727916 | 4/1979 | Germany | |
| 239582 | 6/1924 | United Kingdom | |
| 330474 | 6/1930 | United Kingdom | |
| 994274 | 6/1965 | United Kingdom | |
| 1139715 | 1/1969 | United Kingdom | |
| 1274374 | 1/1972 | United Kingdom | |
| 2223173 | 4/1990 | United Kingdom | 604/349 |
| 2233232 | 1/1991 | United Kingdom | 604/349 |

Primary Examiner—David H. Willse
Attorney, Agent, or Firm—Stuart E. Krieger

[57] ABSTRACT

A retractile penis device comprises an apertured plate carrying an inflatable toroid ring, the ring being substantially aligned with the aperture and acting in use when inflated to apply pressure to the base of the penis and the surrounding skin area of the wearer.

7 Claims, 3 Drawing Sheets

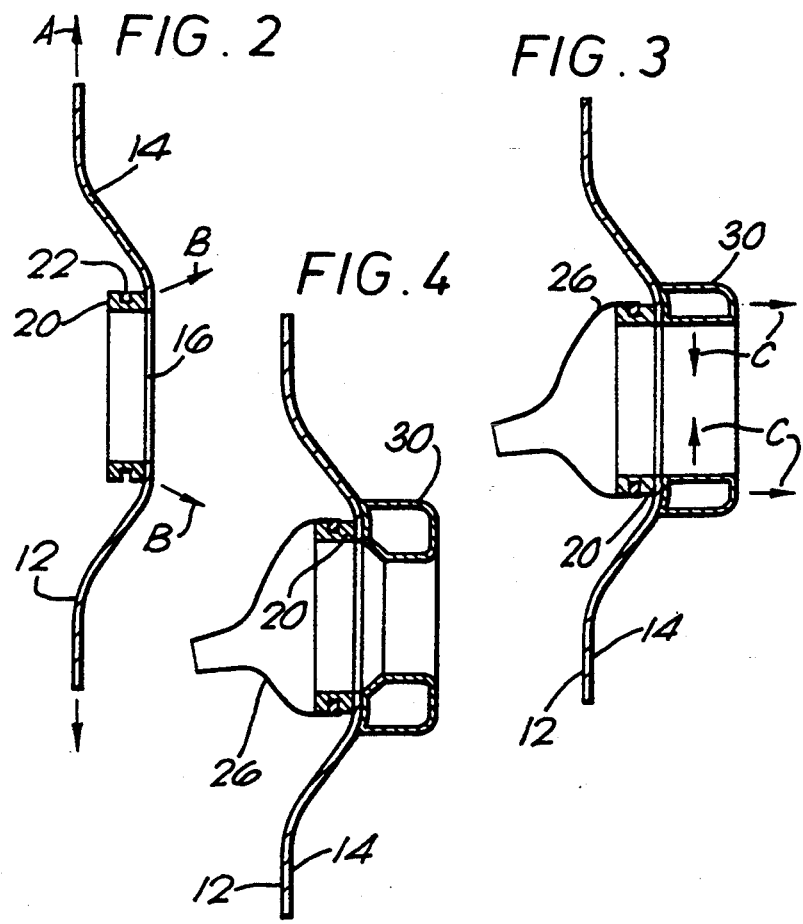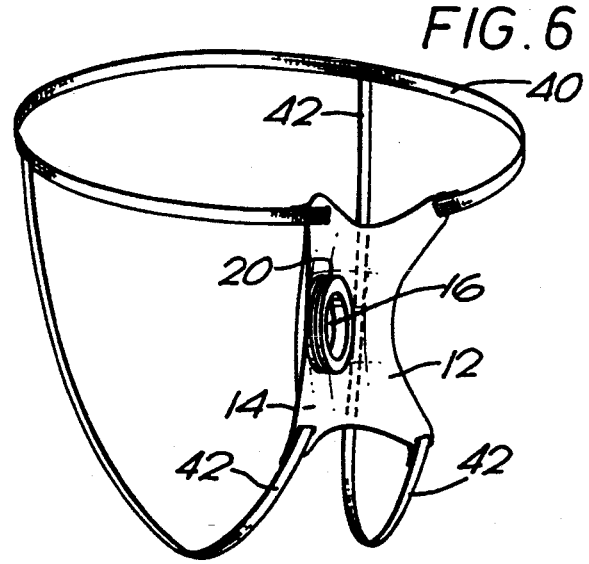

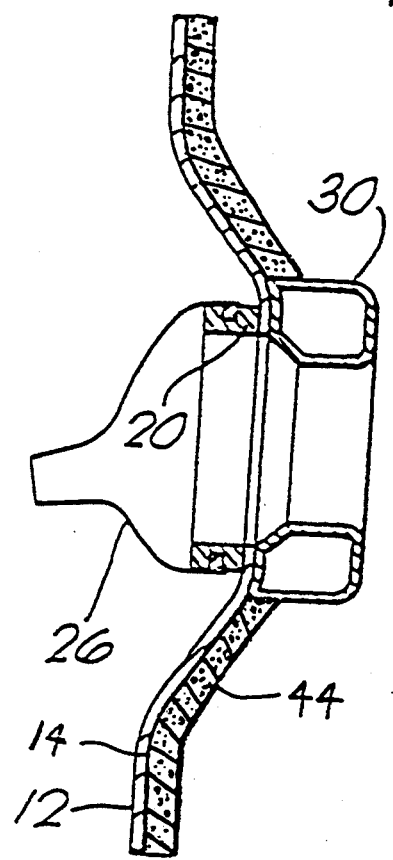

RETRACTILE PENIS DEVICE

This is a continuation of application Ser. No. 07/548,696, filed Jul. 5, 1990, now abandoned.

BACKGROUND OF THE INVENTION

Urinary incontinence can result from a variety of physical or mental dysfunctions. For men this problem can be coped with by employing an indwelling catheter or more commonly in ambulatory patients by use of an external catheter which is adhered to the shaft of the penis by a double sided adhesive strip. This type of system is shown, for example, by Rogers et al. in U.S. Pat. Nos. 3,835,857 and 3,863,638.

Another approach involves an external catheter in combination with specially constructed briefs or harness. Such systems are shown, for example, by Stein in U.S. Pat. No. 4,022,213, by Komis in U.S. Pat. Nos. 4,553,968 and 4,713,066, by Giacalone in U.S. Pat. Nos. 4,568,340 and 4,588,397, by Jensen et al. in U.S. Pat. No. 4,673,401, by Smith in U.S. Pat. No. 4,813,943, by Matsuura in U.S. Pat. Nos. 4,838,883 and 4,886,510, by Terauchi et al. in U.S. Pat. No. 4,820,291, by Salt in U.K. Patent 1,274,374, by Cross in U.K. Patent Application 2,223,173A, by Wirkner in German Offenlengungsschrift 2,727,916, by Ozenne in European Patent 32,138, and by Demoulin in European Patent 119,143.

Other proposals have included inflatable sealing means to secure the external catheter. Such systems are shown, for example, by Carrigan in U.S. Pat. No. 3,353,538, Riotota et al. in U.S. Pat. No. 4,013,077, Paylinch in U.S. Pat. No. 4,239,044, Rogers in U.S. Pat. No. 4,281,648, and Ruffini in U.S. Pat. No. 4,655,755.

In some instances the problem of male urinary incontinence is further complicated because the patient also is suffering from a retractile penis. Such condition occurs frequently in patients who are obese or who have lost muscle control in the lower abdomen and makes it difficult, if not impossible, to successfully attach an external catheter or to employ the male incontinence briefs described above. In many circumstances, a retractile penis is a sufficient problem to prevent normal urination even when the patient would otherwise be continent. Such patients are often forced to rely on diapers as the only way to manage their condition.

SUMMARY OF THE INVENTION

This invention relates to a device for use by persons suffering from a retractile penis.

According to a broad aspect of the invention a retractile penis device comprises an apertured plate carrying an inflatable toroidal ring, the ring being substantially aligned with the aperture and acting in use when inflated to apply pressure to the base of the penis and the surrounding skin area of the wearer.

According to an embodiment of the invention, a device for use by a person suffering from a retractile penis includes an apertured convexlycurved plate, a first attachment ring forming part of or secured to the plate around the aperture whereby a condom-like urine channeling device can have one of its ends sealingly attached to the plate and a second ring on the other side of the plate. The second ring is a hollow toroid and has a port whereby inflation air or gas may be conducted to the interior of the toroid.

The second ring is hence inflatable once the plate is installed on the wearer in the pubic region. When inflated it grips the base of the penis. The possibility of inflation allows a fine adjustment of the pressure which the second ring applies to the area surrounding the base of the penis. It also enhances the security of attachment of the device to the wearer, which is an important point in practice. In this way, the comfort and acceptability in wear can be adjusted to suit the wearer.

The apertured plate may have means other than the stated attachment ring thereon by which a belt or harness can be attached to the plate. In use, the harness holds the plate in towards the abdomen of the wearer. Alternatively the plate may be attached to a suitable garment such as a pair of briefs.

A foam material may be placed on the plate surface that faces towards the skin of the wearer.

The first ring preferably has a peripheral channel in its radially outer surface so that a conventional elasticated mouth of the condom-like urine channelling device can be stretched over and hence sealingly attached to the ring.

The term "convex" when applied to the plate means that the configuration of the plate is such that its projecting or convex surface faces towards the skin of the wearer whereas its concave surface carries the attachment ring.

The plate may be attached in any suitable manner to a pair of briefs, for example, by stitching, by adhesive, or by tabs and cooperating loops.

In a modification of the invention, the first attachment ring is omitted, and a condom-like or other urine-conducting tube is directly attached to the inflatable ring around the periphery of the aperture.

BRIEF DESCRIPTION OF THE DRAWINGS

FIG. 2 is a diagrammatic vertical cross-section through the plate shown in FIG. 4;

FIG. 3 is a cross-sectional view of one example of a device; according to the invention;

FIG. 4 is a cross-sectional view similar to FIG. 3 but showing the toroid in expanded condition;

FIG. 6 is a perspective view of a harness usable with a device according to an embodiment of the invention.

FIG. 7 is a cross-sectional view of another example of the device according to the invention.

DETAILED DESCRIPTION OF THE INVENTION

Figure 1:
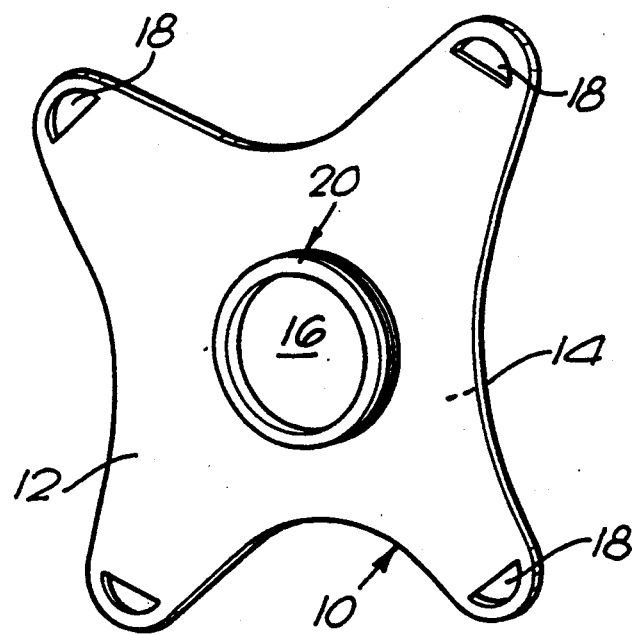
FIG. 1 is a perspective view of a plate embodied in one example of the invention.
Figure 5:
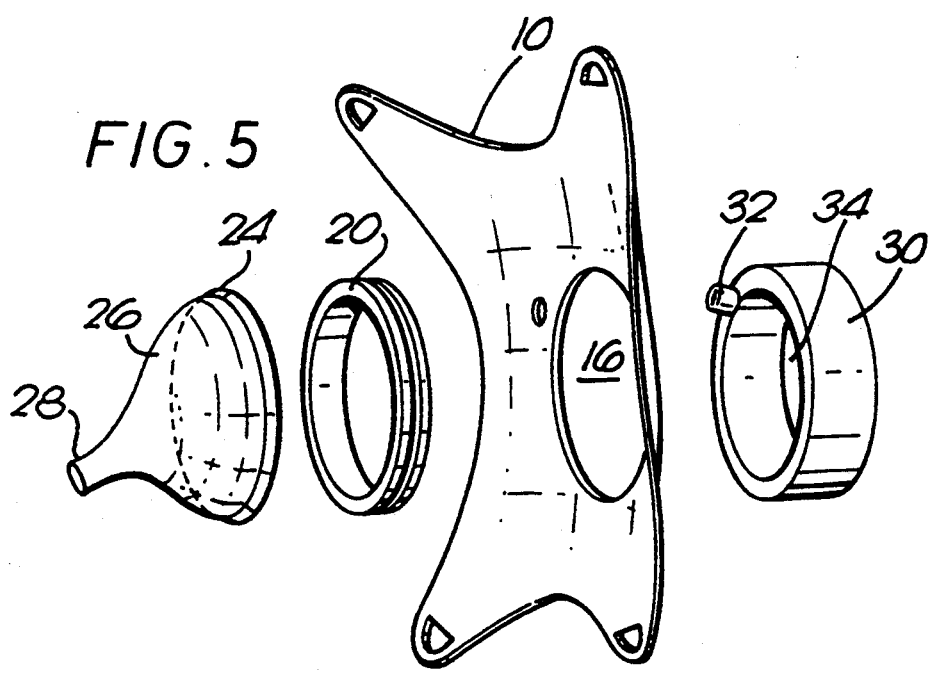
FIG. 5 is an exploded view of the device according to FIG. 4.

Referring firstly to FIGS. 1–5, the illustrated device for use by a person suffering from a retractile penis includes a plate 10 having a front wall 12 and a rear generally convex wall. 14.

The plate has a central aperture 16 for receiving a penis and may be made of a synthetic plastics material, preferably one that is relatively rigid or slightly flexible. The plate has four holes 18 which form a means whereby a belt or harness shown in FIG. 6 can be attached, in order to hold the plate in position on the wearer. In use, the convex surface 14 faces towards the flesh of the wearer surrounding the penis and tends to enhance the extent to which the penis projects from the body. This affect is increased due to the hollow ring 30 which will be described later. At the same time, discomfort is minimised.

The surface 12 of the plate has a ring 20 attached thereto surrounding the aperture 16. The ring 20 has a peripheral channel 22 intended to receive an elasticated rim 24 (see FIG. 5) of a condom-like channelling device 26, whose function is to conduct urine to its outlet 28. The channelling device is not shown in FIGS. 1 and 2.

A hollow toroid 30 is attached to the surface 14 of the plate 10. The toroid has an inlet-outlet port 32 to which can be connected an inflation-deflation tube (not shown) which is connected to a supply of air or gas under pressure. A suitable supply may be obtained using a manually squeezable bulb of the kind used by doctors when measuring blood pressure by an arm band method. The central hole 34 through the toroid 30 is, in use, aligned with the hole 16 in the plate and the end 24 of the condom-like channelling device 26. The toroid 30 and the device 26 are omitted from FIG. 6 for clarity of illustration. In FIG. 6 the waist strap is seen at 40 and the under-leg straps at 42.

In FIG. 2, the force applied by the straps is indicated by the arrows A, and the pressure applied to the wearer by the plate 10 by the arrows B. In FIG. 3 the arrows C similarly indicate the pressure applied.

It will be understood that modifications may be made to the illustrated device without departing from the invention. For example, other shapes of plate 10 could be used. By using a larger toroid 30, adequate results in some cases could be obtained while using a flat plate 10. Any suitable form of inflation-deflation method can be used. To increase lightness and air access to the skin, the plate may be perforated or have multiple apertures.

FIG. 7 shows foam material 44 on the convex surface 14 of the plate 10. The foam material 44 faces the skin of the wearer.

What is claimed is:

1. A device to be worn against the skin in the pubic area of a patient for treatment of a retractile penis comprising:

an apertured plate having a first wall with a rear convex surface for applying pressure against the patient's skin in the pubic area surrounding the penis and a second wall with a front concave surface for facing away from the patient, said second wall opposing said first wall, means for securing said apertured plate to the patient so as to apply pressure by said rear convex surface against the skin in the pubic area surrounding the penis of the patient; and an inflatable toroidal ring having a hole for alignment with said aperture in said plate, said aligned hole and aperture being dimensioned for accommodating a penis therethrough, the penis having a circumferential base portion proximate to its junction with the pubic area, said ring projecting rearwardly from said rear surface so as to contact the base portion of the patient's penis when said plate is secured, said ring applying pressure to the base portion of the penis and surrounding pubic area when said plate is secured and said toroidal ring is inflated.

2. The device of claim 1 further comprising an attachment ring extending frontward from said front concave surface about said aperture, and a tubular sheath secured to said attachment ring.

3. A device according to claim 2 wherein said attachment ring has a radially outer surface and a peripheral channel in said radially outer surface for engaging an end of said tubular sheath.

4. A device according to claim 2 wherein said toroidal ring has a port through which inflation fluid may be conducted while said plate is secured to the patient.

5. A device according to claim 1 wherein said means for securing includes a belt or harness attached to said plate.

6. A device according to claim 1 wherein said means for securing includes an underwear garment.

7. A device according to claim 1 further comprising foam material on said rear convex surface for contacting the skin in the pubic area of the patient.

* * * * *